United States Patent [19]

Ishikawa et al.

[11] Patent Number: 5,145,851
[45] Date of Patent: Sep. 8, 1992

[54] METHOD FOR TREATING URINARY OBSTRUCTION

[75] Inventors: Masayuki Ishikawa, Tokyo; Hiroshi Azuma, Asaka; Shigeru Ito, Yokohama; Tomohiro Yamaguchi, Hitachi, all of Japan

[73] Assignee: Hitachi Chemical Co., Ltd., Tokyo, Japan

[21] Appl. No.: 780,405

[22] Filed: Oct. 17, 1991

Related U.S. Application Data

[63] Continuation of Ser. No. 577,635, Sep. 4, 1990, abandoned.

Foreign Application Priority Data

Sep. 6, 1989 [JP] Japan .................. 1-230750

[51] Int. Cl.$^5$ ............................................. A61K 31/495
[52] U.S. Cl. ............................................. 514/252
[58] Field of Search ................................. 514/252

[56] References Cited

U.S. PATENT DOCUMENTS 3,957,786  5/1976  Klemm et al. ............... 260/256.4 C

FOREIGN PATENT DOCUMENTS 40229  9/1986  Japan .
26517  1/1989  Japan .

OTHER PUBLICATIONS

Patent Abstracts of Japan, vol. 13, No. 108 (C-596) (3556) May 16, 1989.
Berkow et al., "The Merck Manual of Diagnosis and Therapy", 15th Ed. (1987) pp. 1633-1637.
Fortschr. Med., vol. 104, No. 42 (1986) pp. 793-796.
Heilberg et al., Medwelt, vol. 49, No. 83 (1983 pp. 1407-1412).
Iyaku Journal, vol. 24, No. 12, p. 2661 (1988).
Nihon Hinyoki Gakkai-shi, vol. 76, 325-327 (1985).
Iyaku to Yakugaku, vol. 19, 411-429 (1988).

*Primary Examiner*—Frederick E. Waddell
*Assistant Examiner*—Diane Gardner
*Attorney, Agent, or Firm*—Abelman Frayne & Schwab

[57] ABSTRACT

6-[[3-[4-(2-Methoxyphenyl)-1-piperazinyl)propyl]-amino]-1,3-dimethyluracil can be used as a therapeutic agent for urinary obstruction.

1 Claim, No Drawings

METHOD FOR TREATING URINARY OBSTRUCTION

This application is a continuation of application Ser. No. 577,635, filed Sep. 4, 1990, now abandoned.

BACKGROUND OF THE INVENTION

1. Field of the Invention

This invention relates to a method for treating urinary obstruction.

More particularly, it is concerned with a method for treating urinary obstruction which comprises administering a therapeutically effective amount of 6-[[3-[4-(2-methoxyphenyl)-1-piperazinyl]propyl]amino]-1,3-dimethyluracil (also referred to as urapidil) or a pharmaceutically acceptable acid addition salt thereof to a mammal including a human being afflicted with urinary obstruction.

2. Description of the Prior Art

Urinary obstruction includes such symptoms as difficulty in urination, pollakiuria, nocturnal enuresis, incontinence of urine, feeling of residual urine and acute ischuria. These symptoms occur due to a variety of causes, for example, hypertrophy of prostate glands, autonomic imbalance, organic deficiencies of the urinary tracts or nephritis and cystitis caused by infectious microorganisms.

It has been revealed that the urinary obstruction caused by hypertonia of the sympathetic nervous system and prostatauxe among those mentioned above is deeply related to the contraction of smooth muscles via $\alpha_1$-adrenoceptors (for example, Yamaguchi et al.: Iyaku Journal, Vol. 24, No. 12, 1988, p. 2661).

As for hypertrophy of the prostate glands in humans, it is suggested that increase in distribution density of $\alpha_1$-adrenoceptors promotes resistance to urination, because there is observed no change of the sensitivity of $\alpha_1$-adrenoceptors in the prostate glands but marked increase in their distribution density in proportion to hypertrophy of the prostate glands (Yokoyama et al.: Nihon Hinyoki Gakkai-shi, Vol. 76, pp. 325-327, 1985).

Further, efficacy of prazosin which has already been used as an $\alpha_1$-adrenoceptor blocking agent in antihypertensives is clinically evaluated and is being recognized as a therapeutic agent for the urinary obstruction caused by hypertrophy of prostate glands or hypertonia of the sympathetic nervous system (Yamaguchi et al.: Iyaku to Yakugaku, Vol. 19, pp. 411-429, 1988).

Furthermore, certain prazosin-analogous compounds which exhibit a mild antihypertensive action (Japanese Patent Publication No. 40229/1986) have been found to possess an $\alpha_1$-adrenoceptor blocking activity at those sites which play an important role in urination mechanism, and it is proposed that they will be useful not only as a hypotensive agent but also as a therapeutic agent for urinary obstruction (Japanese Patent LOP Publication No. 26517/1989).

However, since these $\alpha_1$-adrenoceptor blocking agents are poorly selective in that they block not only $\alpha_1$-adrenoceptors in tissues of the urinary tracts which play an important role in urination mechanism but also $\alpha_1$-adrenoceptors distributed in blood vessels, there still remain problems of side effects such as orthostatic hypotensive asthenia. Thus, a therapeutic agent without such side effects is demanded. Particularly, $\alpha_1$-adrenoceptor blocking agents which are less active on the $\alpha_1$-adrenoceptors distributed in blood vessels but highly active on the $\alpha_1$-adrenoceptors distributed in the lower urinary tracts, for example, the prostate gland, internal urethral sphicter muscle and trigonum vesicae, would be useful as agents for treating urinary obstruction without fear of said side effects. In this respect, it is a subject to develop, as a therapeutic agent for urinary obstruction, $\alpha_1$-adrenoceptor blocking agents possessing such properties.

SUMMARY OF THE INVENTION

As a result of extensive studies to solve the above subject we have found that 6-[[3-[4-(2-methoxyphenyl)-1-piperazinyl]propyl]amino]-1,3-dimethyluracil represented by formula (I)

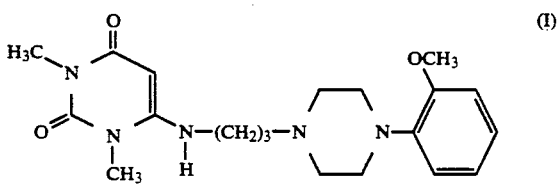

is selectively active on the $\alpha_1$-adrenoceptor in the urinary tracts and that it is useful as an agent for treating urinary obstruction with no fear of the above-mentioned side effects. The present invention is based upon the above finding.

Thus, the invention relates to an agent for treating urinary obstruction which comprises an effective amount of 6-[[3-[4-(2 methoxyphenyl)-1-piperazinyl]propyl]amino]-1,3-dimethyluracil represented by the above-mentioned formula (I) or a pharmaceutically acceptable acid addition salt thereof.

6-[[3-[4-(2-Methoxyphenyl)-1-piperazinyl]propyl]amino]-1,3-dimethyluracil of formula (I) is a known compound synthesized by K. Klemm et al. and proposed in U.S. Pat. No. 3,957,786 with disclosure of its usefulness as an antihypertensive agent. It is however a new finding that the compound is selectively active on the $\alpha_1$-adrenoceptor in tissues of the urinary tracts and is useful as a therapeutic agent for urinary obstruction.

The above-mentioned 6-[[3-[4-(2-methoxyphenyl)-1-piperazinyl]propyl]amino]-1,3-dimethyluracil of formula (I) was tested by us for the $\alpha_1$-adrenoceptor blocking activity both in blood vessels and in the lower urinary tracts. We have compared these activities and investigated tissue-selectivity of the $\alpha_1$-adrenoceptor blocking activity. As a result of the investigation, the above-mentioned compound is found to possess a selectively blocking activity on the $\alpha_1$-adrenoceptor distributed in the lower urinary tracts. Therefore, unlike prior $\alpha_1$-adrenoceptor blocking agents such as prazosin used as a therapeutic agent for urinary obstruction, the above-mentioned compound can be used as a therapeutic agent for urinary obstruction free from side effects such as orthostatic hypotensive asthenia.

As the acid addition salts, there can be mentioned mineral acid salts such as the hydrochloride, sulfate, hydrobromide and phosphate, and organic acid salts such as the oxalate, acetate, lactate, succinate, citrate, tartrate, maleate, fumarate and malate.

The agent for treating urinary obstruction according to the invention can be administered orally, for example, as tablets, capsules, granules, powders or syrup, parenterally as suppositories, by intravenous or subcutaneous injection of a injectable preparation, or percutaneously, as ointment.

The tablets are prepared by compressing or forming the active ingredient together with additional adjuvant component. As the adjuvant component may be used a pharmaceutically acceptable excipient such as binder (e.g. corn starch), filler (e.g. lactose, microcrystalline cellulose), disintegrating agent (e.g. sodium starch-glycolate), lubricant (e.g. magnesium stearate) or wetting agent (e.g. sodium laurate). The tablets may also be coated.

Liquid preparations such as syrup, solution or suspension can be prepared by a conventional method, for example, using a suspending agent (e.g. methylcellulose), an emulsifier (e.g. lecithin) or a preservative.

The injectable preparation may be in the form of solution, suspension, or oily or aqueous emulsion and may contain a suspension stabilizer, a dispersing agent or the like.

Although a dosage of the drug is variable depending upon the form of administration, symptoms, age and bodyweight of the patient, it is preferable in oral administration to give 0.1 mg–300 mg per day in 1–3 divided doses in adults.

EXAMPLE

The following examples are given to demonstrate that 6-[[3-[4-(2-methoxyphenyl)-1-piperazinyl]propyl]amino]-1,3-dimethyluracil represented by formula (I) possesses a selectively blocking action on $\alpha_1$-adrenoceptor distributed in the lower urinary tracts and that it can be used for the therapy of urinary obstruction caused by hyperactivity of the $\alpha_1$-adrenoceptor in the lower urinary tracts without side effects such as orthostatic hypotension.

In the examples, the effect of the compound of formula (I) is shown in comparison with a known drug, prazosin.

EXAMPLE 1

Comparison of $\alpha_1$-Adrenoceptor-Blocking Activity in the Smooth Muscle of Trigonum Vesicae and Thoracic Aorta Among Test Drugs Male albino rabbits weighing 2.2–2.5 kg were intravenously given pentobarbital (Nembutal ® manufactured by Abbott) at a dose of 35 mg/kg bodyweight and sacrificed by exsanguination. The thoracic aorta and urinary bladder were rapidly excised and placed in modified Krebs solution. After removal of fat and unnecessary connective tissue, helical strips (3×15 mm in size) of the thoracic aorta and longitudinal strips (3×15 mm in size) of trigonum vesicae were prepared and used as specimen. The helical strips were carefully denuded of endothelium attached thereto in order to avoid any effect of the endothelium-derived vascular relaxing factors.

The preparations were vertically mounted in an organ bath filled with 20 ml of the modified Krebs solution (aerated with a gas mixture of 95 vol % of oxygen and 5 vol % of carbon dioxide and kept at 37° C.). The other end of each strip was attached to a transducer for tension measurement (the model TB-611T manufactured by Nihon Kohden Kogyo K.K.). Changes in tension were recorded on a pen-writing oscillograph (the model Wi-681G manufactured by Nihon Kohden Kogyo K.K.). Composition of the modified Krebs solution used herein was as follows: NaCl 115.0, KCl 4.7, MgSO$_4$·7H$_2$O 1.2, CaCl$_2$·2H$_2$O 2.5, KH$_2$PO$_4$ 1.2, NaHCO$_3$ 25.0 and glucose 10.0 (concentration in mM). The solution contained $10^{-6}$ M propranolol, a $\beta$-adrenoceptor blocker (manufactured by Sigma). The loading tension was adjusted to attain a weight of 2 g for aorta and a weight of 1 g for trigone. The strips were allowed to equilibrate for at least 60 min. before initiation of the experiment, and during this period the modified Krebs solution in the organ bath was replaced every 20 min.

First, noradrenaline (manufactured by Sigma, $10^{-6}$–$10^{-4}$ M) was cumulatively added to each specimen to prepare a concentration-response curve to noradrenaline (to determine the 50% effective concentration ED$_{50}$). Next, in order to assess the $\alpha_1$-adrenoceptor-blocking activity of various test drugs, noradrenaline was cumulatively added in the same way as above to each specimen in the presence of the compound of formula (I), or in the presence of prazosin as a control drug to prepare a concentration-response curve to noradrenaline. The results were analyzed by Schild plotting to determine pA$_2$ (reciprocal of the log of concentration of the blocking agent necessary for parallel shift of the noradrenaline-induced contraction to a concentration two fold as high). The results are shown in Table 1.

The compound of formula (I) exhibited a larger pA$_2$ in trigonum vesicae. In other words, the noradrenaline contraction was inhibited in a lower concentration. On the contrary, the pA$_2$ was smaller in the thoracic aorta. Thus, as the noradrenaline contraction is inhibited in the thoracic aorta only in a relatively high concentration, it can be said that selectivity of the compound of formula (I) toward trigonum vesicae is about 9 times higher than that toward the thoracic aorta.

It is noted that prazosin shows a larger pA$_2$ in the thoracic aorta than in the trigonum vesicae, and consequently shows higher selectivity in the thoracic aorta than in trigonum vesicae.

TABLE 1

| | Comparative selectivity of the $\alpha_1$-adrenoceptor blocking activity | | |
|---|---|---|---|
| | pA$_2$* | | |
| Compound | Thoracic aorta | Trigonum vesicae | Activity ratio** |
| Compound I | 6.33 (±0.11) | 7.28 (±0.04) | 8.91 |
| Prazosin | 8.52 (±0.01) | 8.25 (±0.05) | 0.53 |

*The result is expressed in terms of the mean value (± standard error).
**The activity ratio is expressed in terms of the ratio of pA$_2$ (calculated as concentration in all cases) with trigonum vesicae as specimen to pA$_2$ with the thoracic aorta as specimen.

EXAMPLE 2

Effect of the Test Drugs on the Maximum Bladder Pressure on Urination

The drugs were tested using rats for the effect on the maximum bladder pressure on urination.

Normal male rats weighing 300–350 g were anesthetized with urethane and laparotomized to expose the bladder. A small opening was formed at the top of the bladder, through which a polyethylene tube was inserted and then ligated. The other end of the polyethylene tube was connected to a three way-stop cock, one way of which was connected to a pressure transducer to record bladder pressure changes on a polygraph and the other way of which was connected to an infusion pump through which was continuously introduced physiological saline solution at a physiological filling rate of 0.05 ml/min.

First, the maximum bladder pressure was measured when the first urination after initiation of the continuous infusion of the physiological saline solution was observed. Next, after a predetermined period of time, the test drug (the compound of formula (I)) or prazosin for comparison diluted with a 5 w/v % of glucose solution was administered to the rat via the femoral vein simultaneously with initiation of continuous infusion of a physiological saline solution. The maximum bladder pressure was similarly measured when the first urination was observed. The ureters had been ligated and cut on the kidney side in order to eliminate the influence of retention of urine.

Blood-pressure were measured simultaneously with the measurement of bladder pressure by inserting one end of a polyethylene tube with ligation into the carotid artery and connecting the other end to a transducer.

Table 2 shows changes of the maximum bladder pressure and blood pressure when the first urination after administration of the drug was observed in terms of the ratio (%) to the value prior to the administration.

The results in Table 2 clearly indicate that whereas the comparative drug prazosin continuously reduces blood pressure and does not reduce maximum bladder pressure at the tested dose, the compound of formula (I) has an effect of reducing maximum bladder pressure, thus a urination-promoting effect with a transient blood-pressure reduction associated.

TABLE 2

| Compound | Dose μg/kg | Maximum bladder pressure (%) | Reduction in blood pressure (%) |
|---|---|---|---|
| Compound I | 3 | 105 (±5) | 0 |
|  | 30 | 93 (±8) | 4.8 (±1.2) |
|  | 100 | 89 (±4) | 16.1 (±1.5) |
| Prazosin | 3 | 102 (±8) | 23.6 (±3.6) |
| Glucose (5%) |  | 104 (±4) | 0 |

*Shown by mean value (± standard error).

EFFECT OF THE INVENTION

As 6-[[3-[4-(2-methoxyphenyl)-1-piperazinyl]-propyl]amino]-1,3-dimethyluracil of formula (I) or a pharmaceutically acceptable acid addition thereof has a selectively blocking activity of $\alpha_1$-adrenoceptors distributed in the lower urinary tracts as compared with $\alpha_1$-adrenoceptors distributed in blood vessels, it is expected that the compound will be useful for the therapy of urinary obstruction caused by hyperactivity of the $\alpha_1$-adrenoceptors distributed in the lower urinary tracts rarely accompanying side effects such as orthostatic hypotension.

What is claimed is:

1. A method for treating urinary obstruction with limited associated reduction in blood pressure which comprises administering a therapeutically effective amount of 6-[[3-[4-(2-methoxyphenyl)-1-piperazinyl]-propyl]amino]-1,3-dimethyluracil represented by formula (I)

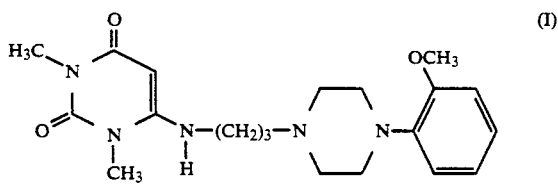

or a pharmaceutically acceptable acid addition salt thereof to a mammal including a human being afflicted with urinary obstruction.

* * * * *